United States Patent
Yun et al.

(10) Patent No.: US 10,773,975 B2
(45) Date of Patent: Sep. 15, 2020

(54) STERILIZATION STRUCTURE OF WATER OUTLET AND WATER TREATMENT DEVICE CONTAINING SAME

(71) Applicant: COWAY CO., LTD., Chungcheongnam-do (KR)

(72) Inventors: Sung-Han Yun, Seoul (KR); Hyoung-Min Moon, Seoul (KR); Won-Il Joo, Seoul (KR); Tae-Seong Kwon, Seoul (KR); Sang-Hyeon Kang, Seoul (KR)

(73) Assignee: Coway Co., Ltd. (KR)

( * ) Notice: Subject to any disclaimer, the term of this patent is extended or adjusted under 35 U.S.C. 154(b) by 175 days.

(21) Appl. No.: 15/756,885

(22) PCT Filed: Sep. 1, 2016

(86) PCT No.: PCT/KR2016/009783
§ 371 (c)(1),
(2) Date: Mar. 1, 2018

(87) PCT Pub. No.: WO2017/039347
PCT Pub. Date: Mar. 9, 2017

(65) Prior Publication Data
US 2018/0244542 A1  Aug. 30, 2018

(30) Foreign Application Priority Data
Sep. 1, 2015  (KR) .................. 10-2015-0123641

(51) Int. Cl.
*A61L 2/10* (2006.01)
*B01D 35/04* (2006.01)
(Continued)

(52) U.S. Cl.
CPC .................... *C02F 1/32* (2013.01); *A61L 2/10* (2013.01); *B01D 35/04* (2013.01); *C02F 9/005* (2013.01);
(Continued)

(58) Field of Classification Search
CPC ...... A61L 2/10; B01D 35/04; B01D 2259/804; B67D 2210/0001; B67D 2210/00015;
(Continued)

(56) References Cited

U.S. PATENT DOCUMENTS

| 2006/0213928 A1 | 9/2006 | Ufheil et al. |
| 2011/0165019 A1 | 7/2011 | Green |

(Continued)

FOREIGN PATENT DOCUMENTS

| CN | 1817780 | 8/2006 |
| CN | 102137683 | 7/2011 |

(Continued)

OTHER PUBLICATIONS

PCT/ISA/210 Search Report issued on PCT/KR2016/009783 pp. 4.
(Continued)

*Primary Examiner* — Lucas A Stelling
(74) *Attorney, Agent, or Firm* — The Farrell Law Firm, P.C.

(57) ABSTRACT

Disclosed are a sterilizing structure of a water outlet and a water treatment apparatus including the same. The sterilizing structure of the water outlet according to an embodiment of the present invention may comprise a water outlet for discharging treated water treated in a water treatment device externally, and a sterilizer for sterilizing the water outlet.

17 Claims, 12 Drawing Sheets

(51) Int. Cl.
  *C02F 1/32* (2006.01)
  *C02F 1/44* (2006.01)
  *C02F 9/00* (2006.01)

(52) U.S. Cl.
  CPC ............ *B01D 2259/804* (2013.01); *B67D 2210/0001* (2013.01); *B67D 2210/00015* (2013.01); *C02F 1/441* (2013.01); *C02F 2301/04* (2013.01); *C02F 2307/00* (2013.01); *C02F 2307/10* (2013.01)

(58) Field of Classification Search
  CPC .. C02F 1/32; C02F 1/441; C02F 9/005; C02F 2301/04; C02F 2307/00; C02F 2307/10
  See application file for complete search history.

(56) References Cited

U.S. PATENT DOCUMENTS

2014/0086565 A1* 3/2014 Lilley .................... B67D 1/10
  392/449

2015/0217984 A1 8/2015 Orita

FOREIGN PATENT DOCUMENTS

| | | |
|---|---|---|
| CN | 102935992 | 2/2013 |
| CN | 203943527 | 11/2014 |
| CN | 104640803 | 5/2015 |
| JP | 5-26900 | 4/1993 |
| KR | 1020100131802 | 12/2010 |
| KR | 1020140070016 | 6/2014 |
| KR | 1020140096589 | 8/2014 |
| KR | 1020150042469 | 4/2015 |
| KR | 1020150056280 | 5/2015 |

OTHER PUBLICATIONS

Chinese Office Action dated Dec. 21, 2018 issued in counterpart application No. 201680050705.1, 9 pages.

Korean Office Action dated Oct. 10, 2018 issued in counterpart Application No. 10-2015-0123642, 5 pages.

* cited by examiner

[Figure 1]
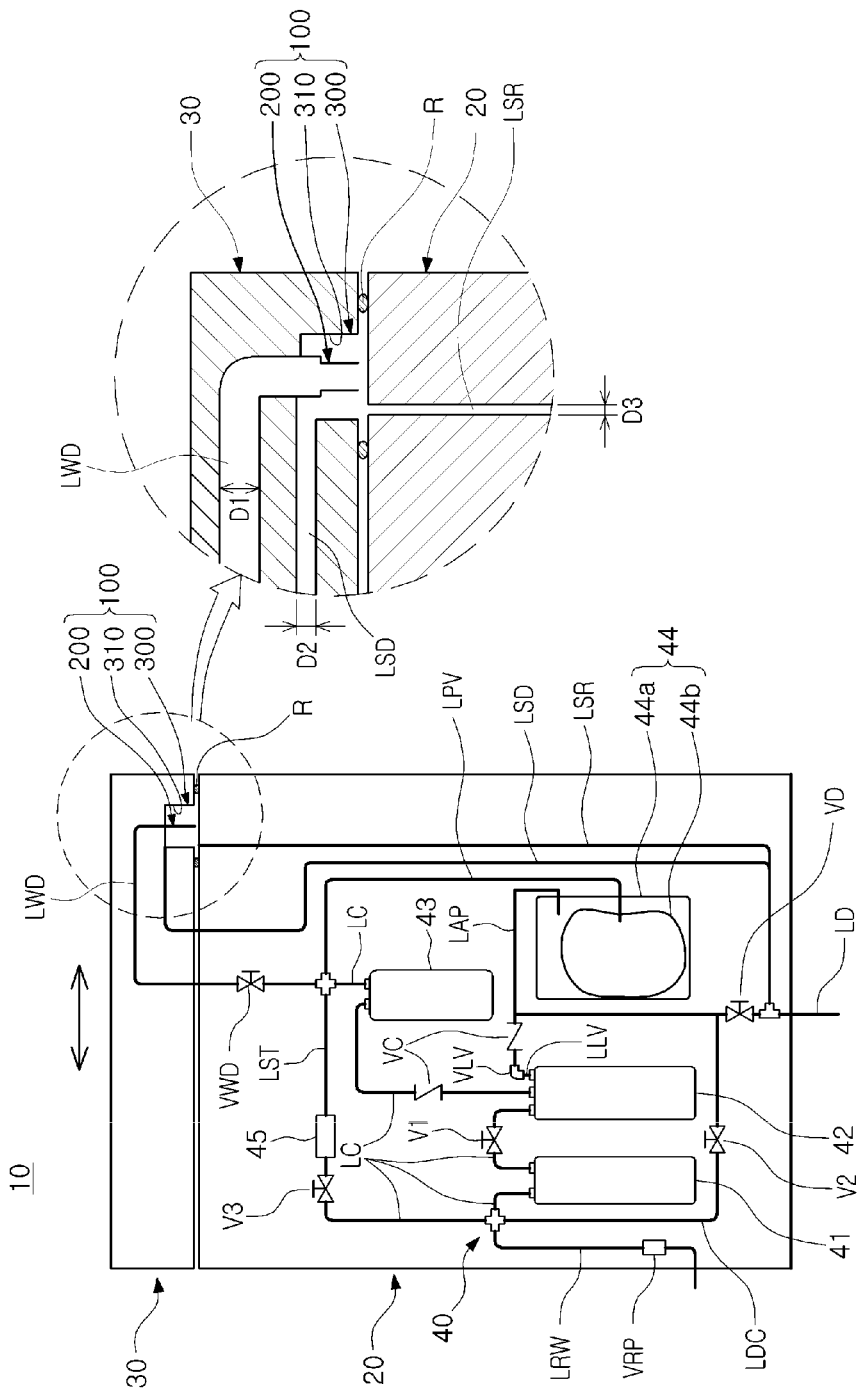

[Figure 2]
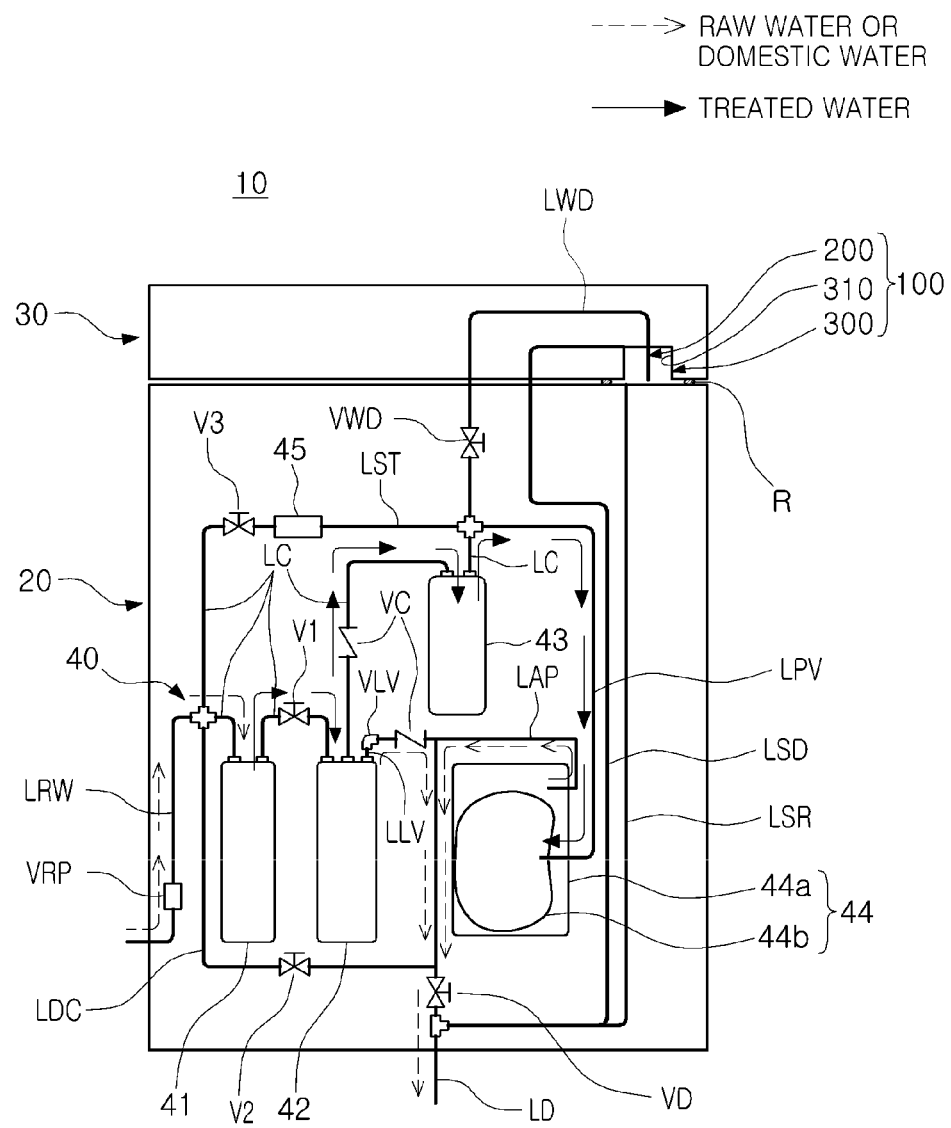

[Figure 3]
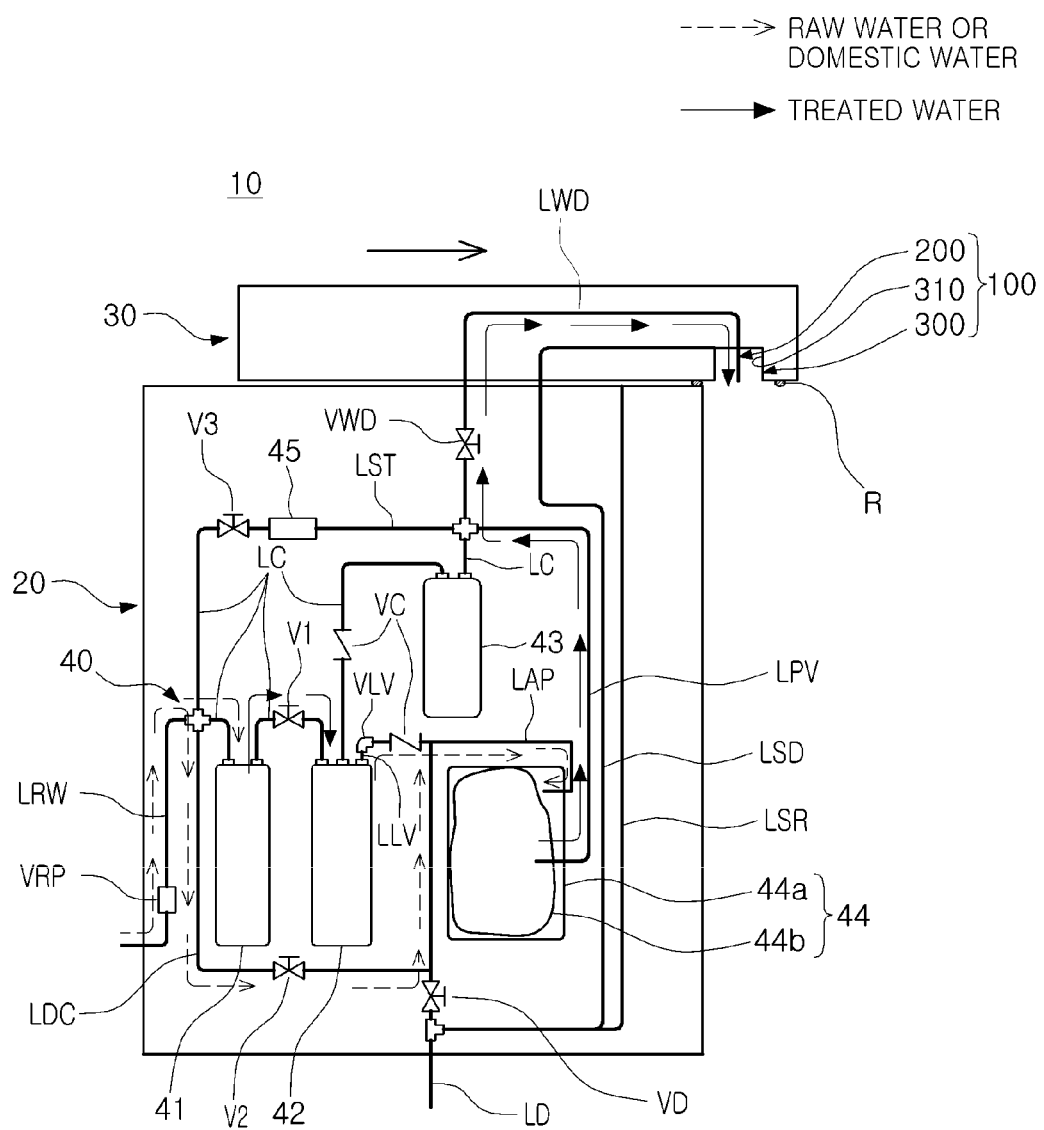

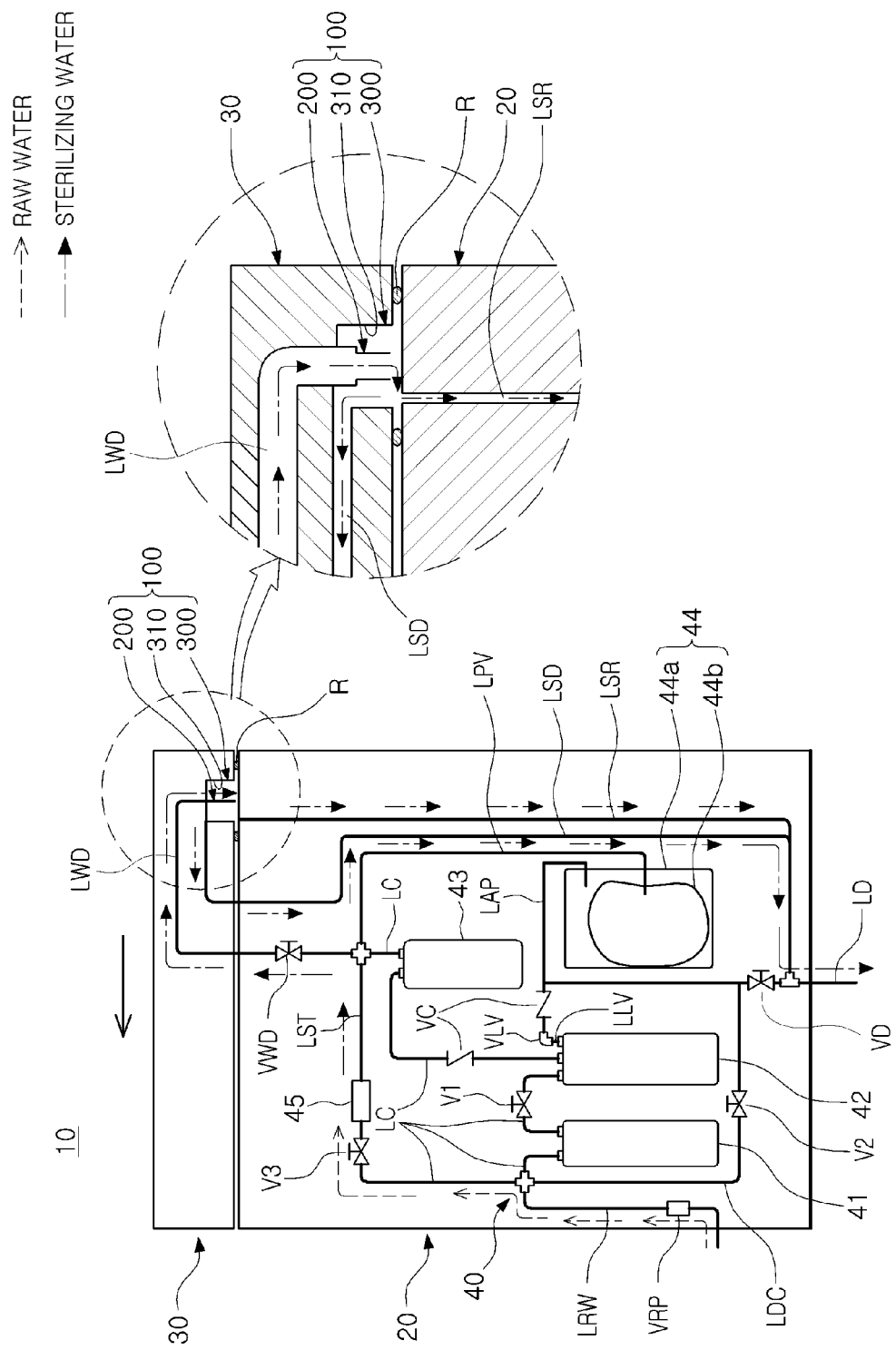
[Figure 4]

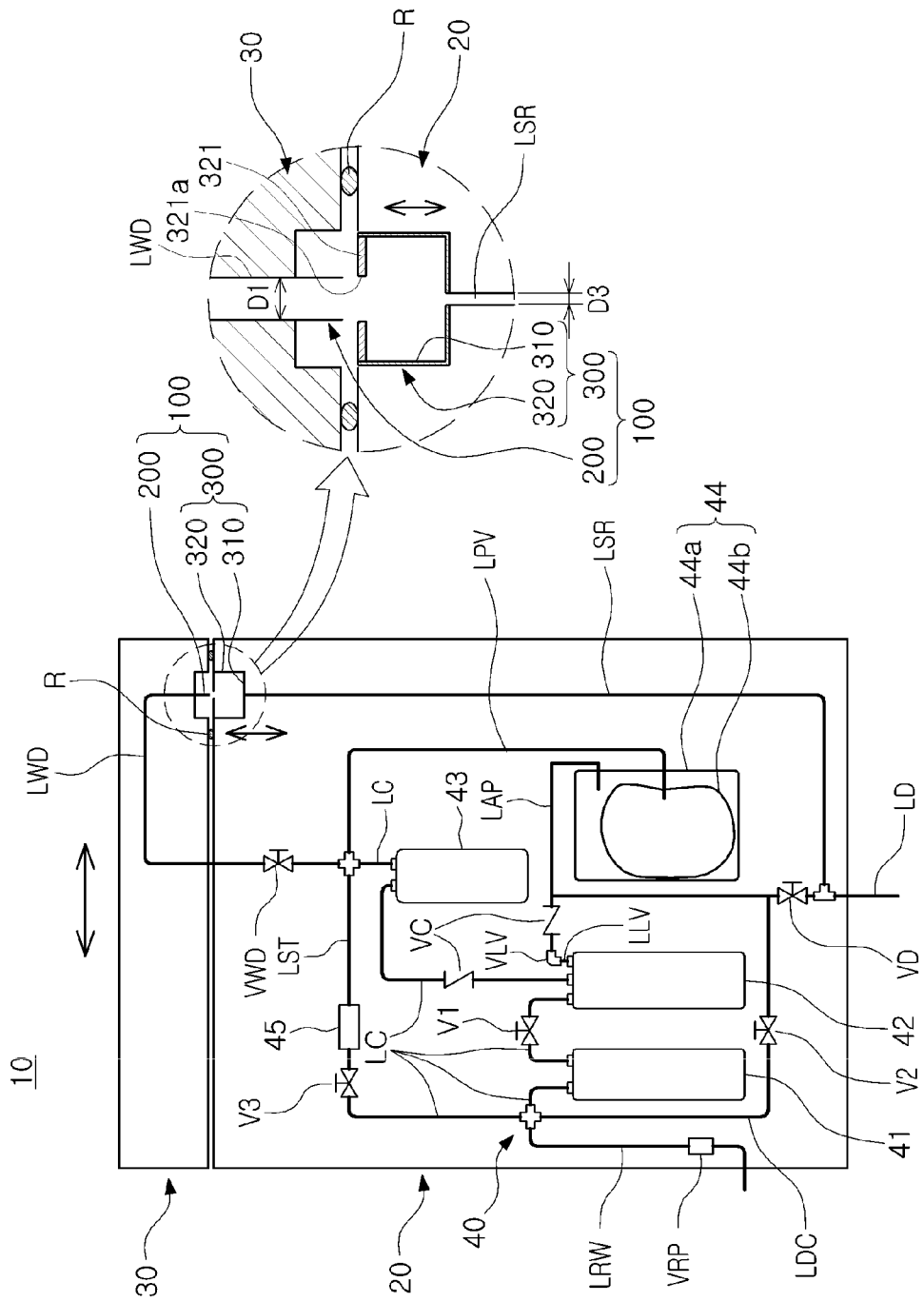
[Figure 5]

【Figure 6】
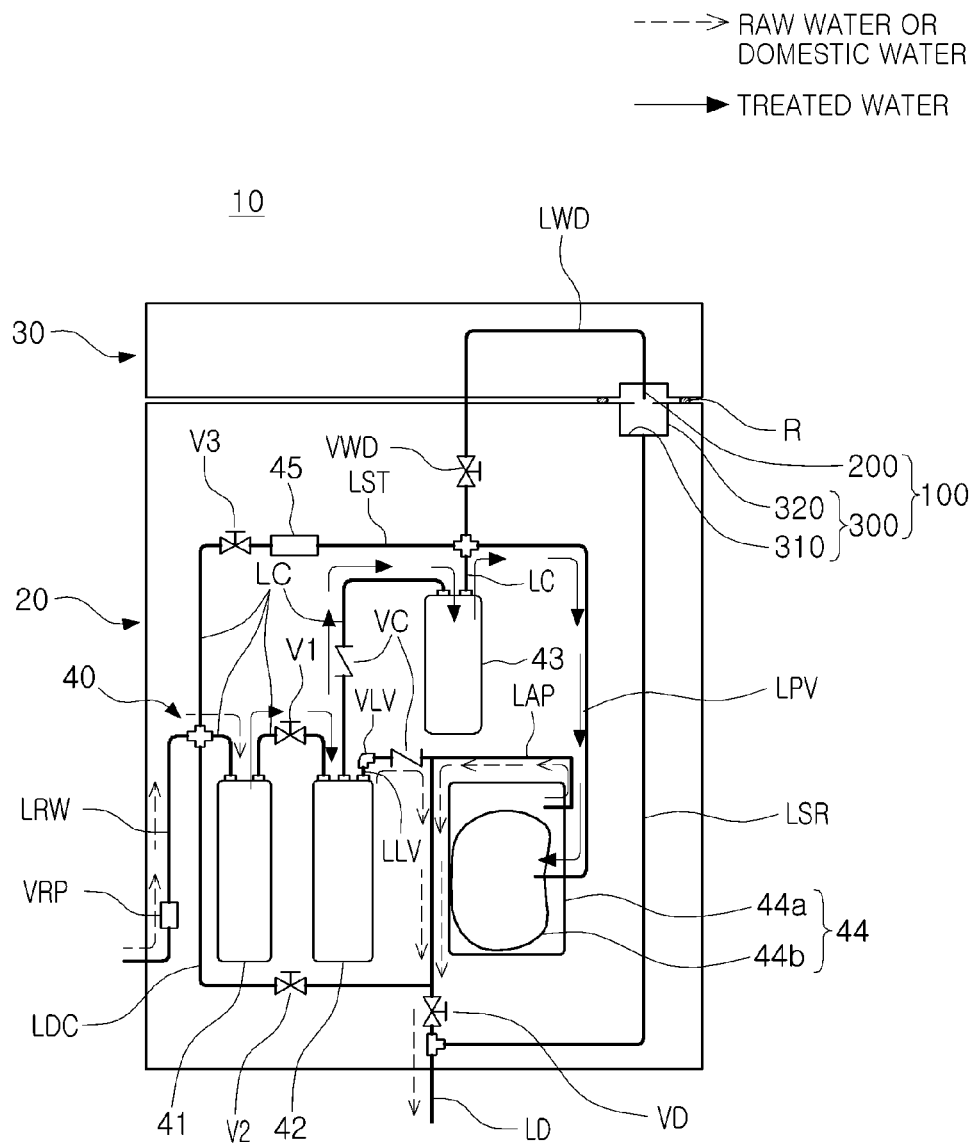

[Figure 7]
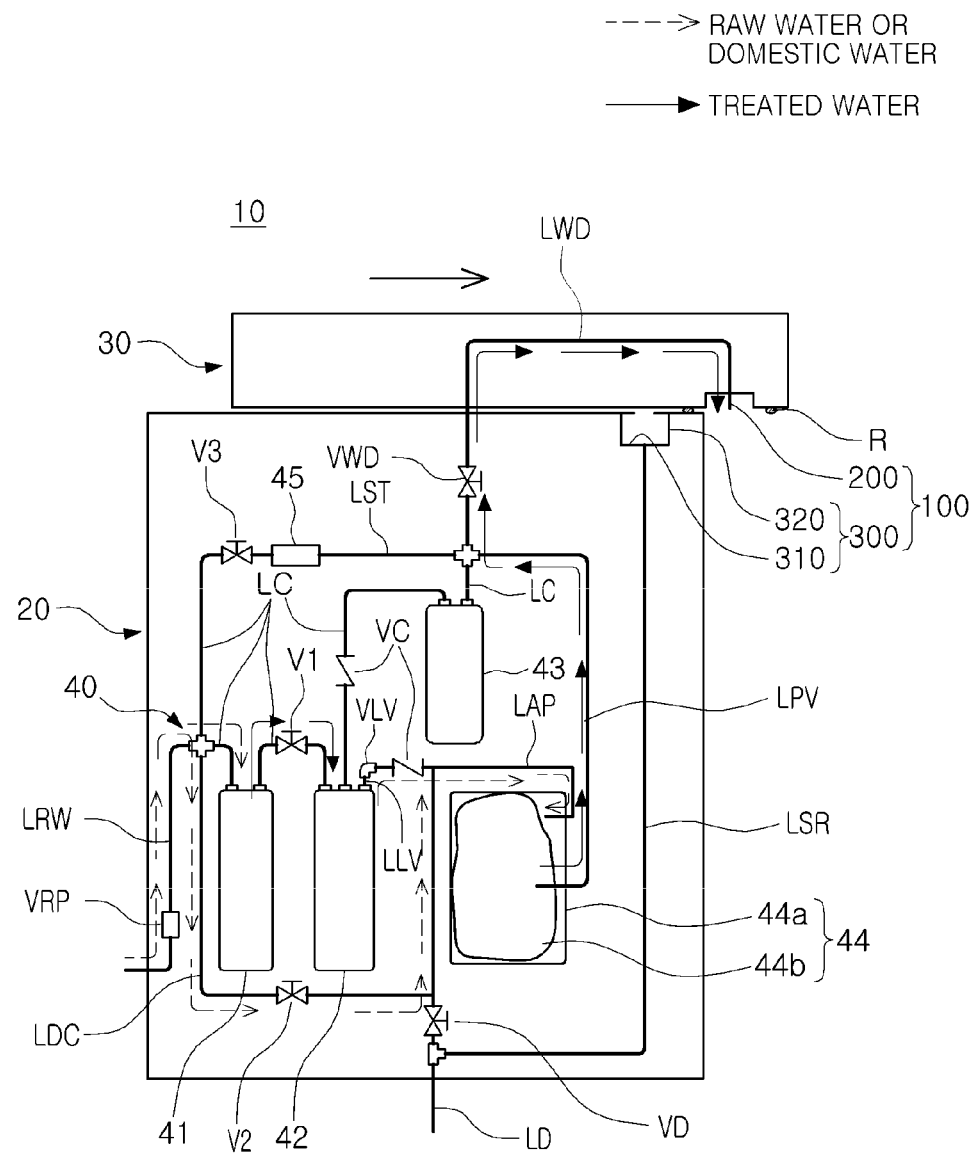

[Figure 8]
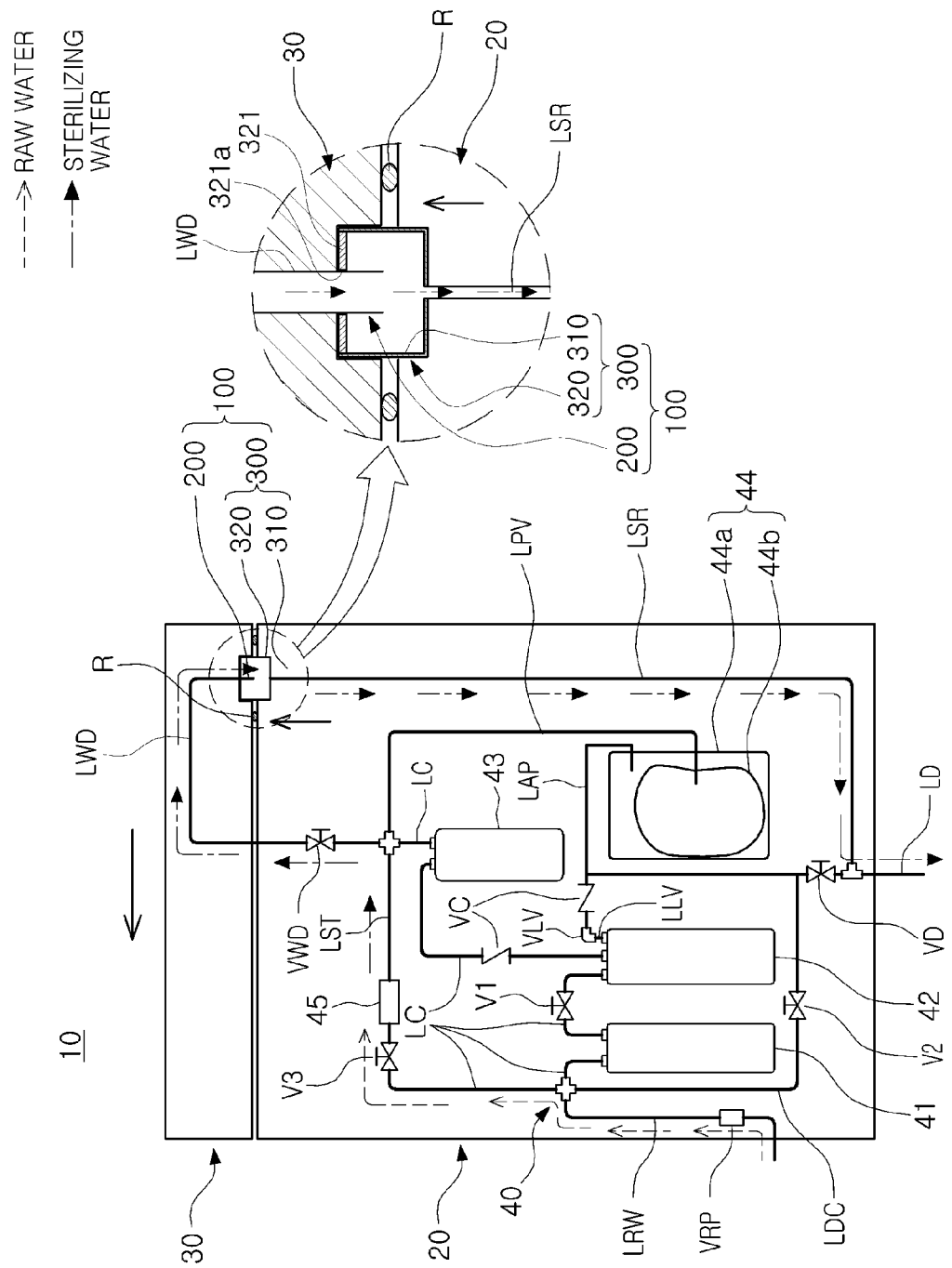

[Figure 9]
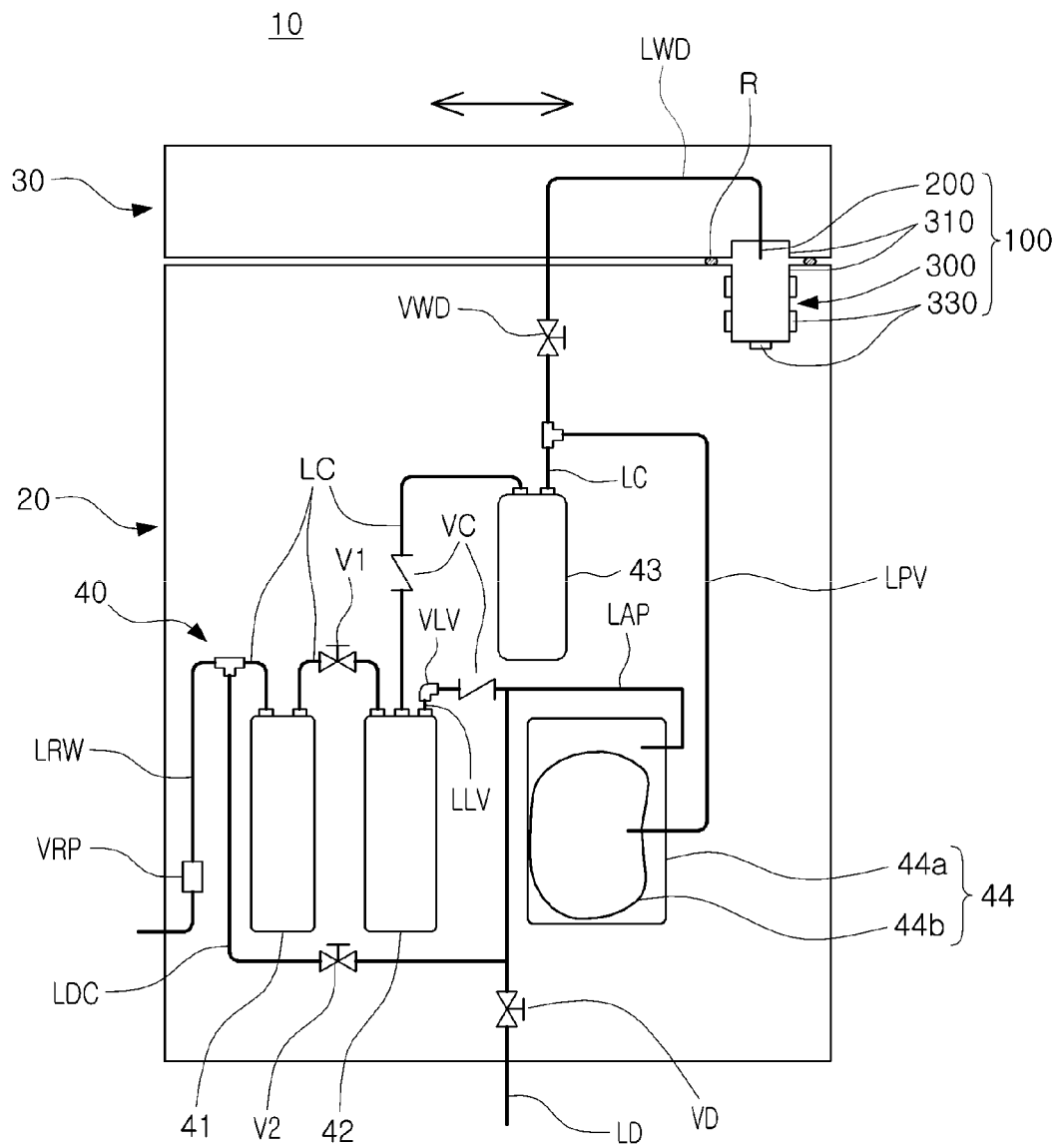

[Figure 10]
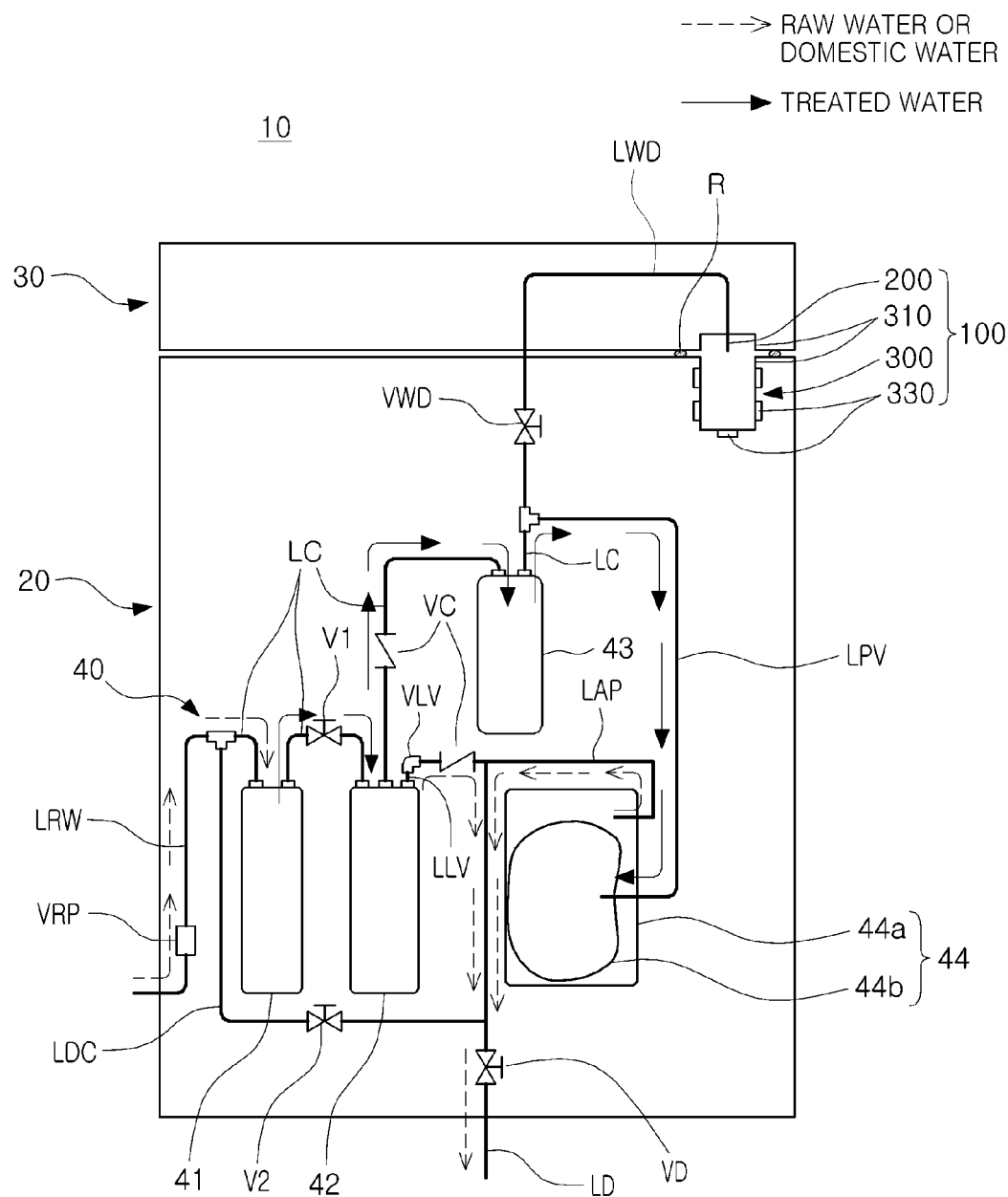

【Figure 11】
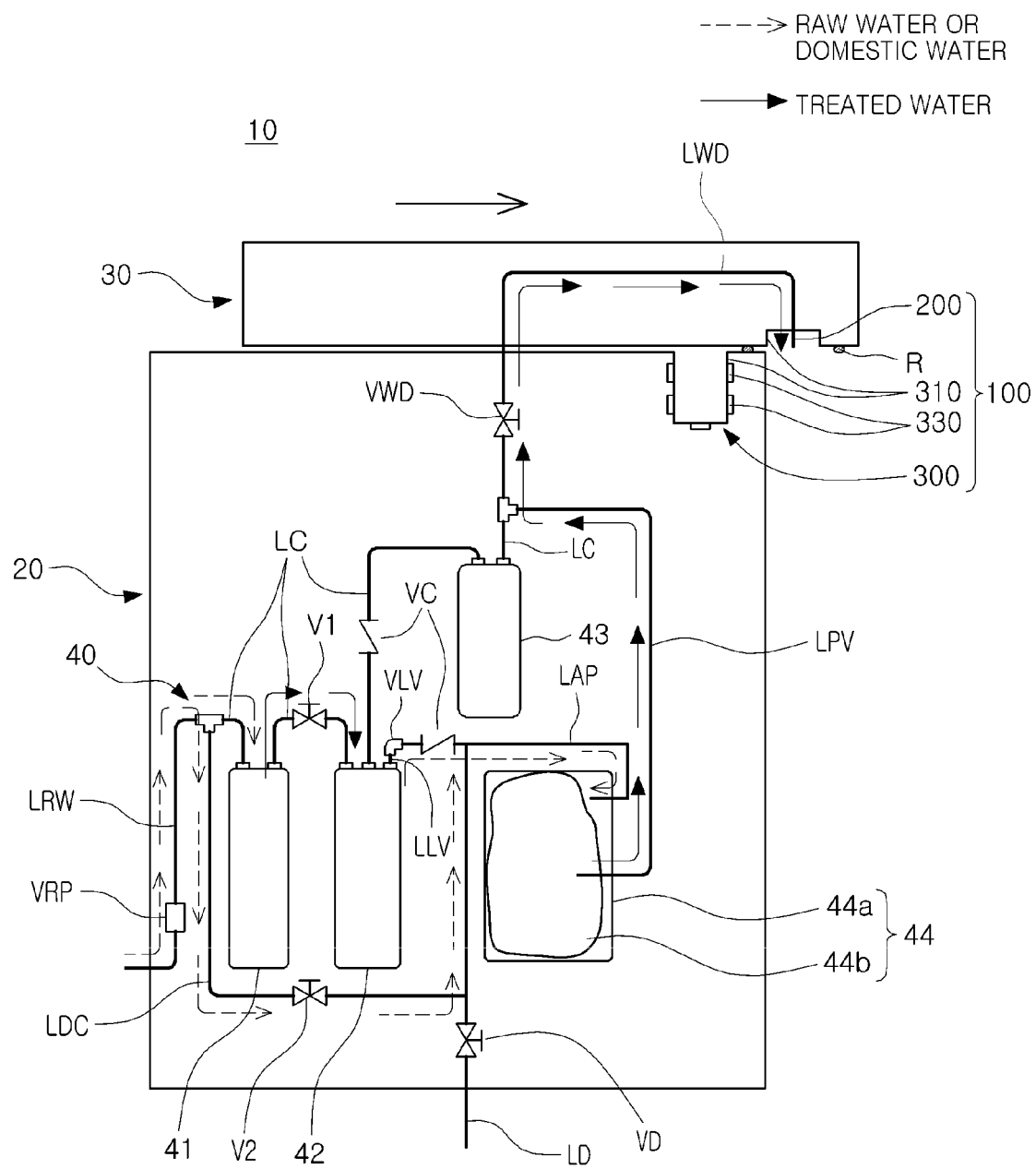

[Figure 12]
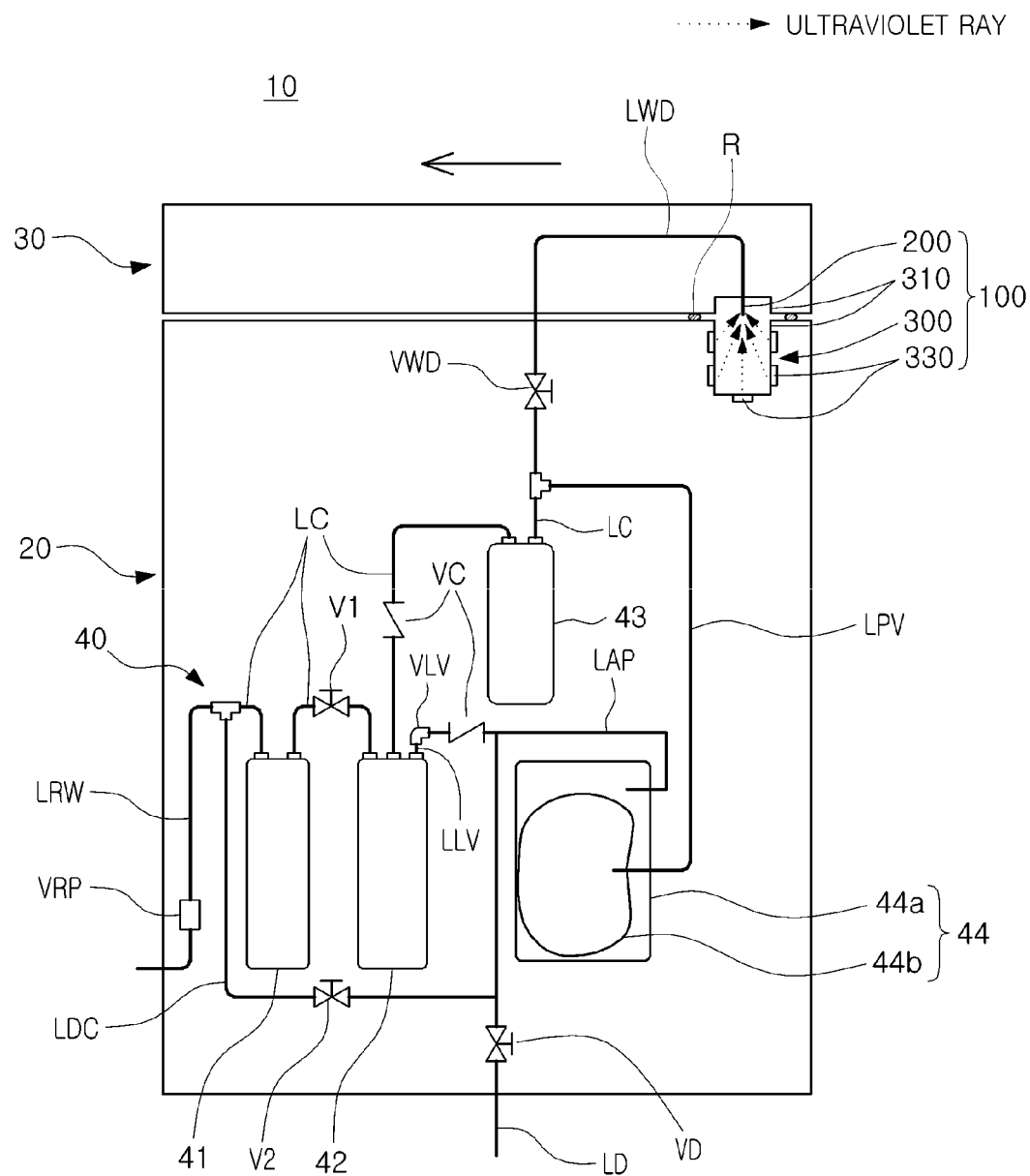

STERILIZATION STRUCTURE OF WATER OUTLET AND WATER TREATMENT DEVICE CONTAINING SAME

PRIORITY

This application is a National Phase Entry of International Application No. PCT/KR2016/009783, which was filed on Sep. 1, 2016, and claims priority to Korean Patent Application Nos. 10-2015-0123641 and 10-2015-0123642, which each were filed on Sep. 1, 2015, the contents of each of which are incorporated herein by reference.

TECHNICAL FIELD

The present disclosure relates to sterilizing structure for sterilizing a water outlet through which water is discharged externally, and a water treatment apparatus including the same.

BACKGROUND ART

A water outlet is installed in a water treatment apparatus or the like to discharge water, e.g. treated water, treated in the water treatment apparatus, externally.

The treated water treated in the water treatment apparatus is discharged through the water outlet and supplied to a user.

A water outlet known in the art may be constantly externally exposed. Accordingly, the water outlet easily becomes contaminated, and sanitary properties of the water outlet may be degraded.

When the water outlet is contaminated, water discharged through the water outlet may also be contaminated and the contaminated water may be supplied to a user.

DISCLOSURE

Technical Problem

Aspects of the present disclosure are to address the above mentioned problems and/or disadvantages and to provide at least the advantages described below.

An aspect of the present disclosure is to improve sanitary properties of a water outlet.

Another aspect of the present disclosure is to sterilize the water outlet.

Another aspect of the present disclosure is to minimize contamination of the water outlet.

Another aspect of the present disclosure is to minimize exposure of the water outlet externally.

Technical Solution

According to an aspect of the present disclosure, there is provided a sterilizing structure of a water outlet device and a water treatment apparatus including the same.

According to an aspect of the present disclosure, a sterilizing structure of a water outlet device may include a water outlet configured to discharge treated water, treated in a water treatment apparatus, externally, and a sterilizer sterilizing the water outlet.

In this case, the water outlet may be located in a moving part configured to move on a main body included in the water treatment apparatus.

Also, the water outlet may be exposed or may not be exposed externally, depending on a movement of the moving part.

In addition, the water outlet may be exposed externally when the treated water treated in the water treatment apparatus is discharged externally, and may not be exposed externally when the treated water is sterilized by the sterilizer or not discharged externally.

In addition, the water outlet may be connected to a discharge line connected to a water treatment part located in the main body to treat raw water flowing into the main body.

In addition, the sterilizer is located in at least one of the main body and the moving part.

In addition, the sterilizer includes a sterilizing space in which the water outlet is sterilized.

In addition, the sterilizing space may be formed in at least one of the main body and moving part included in the water treatment apparatus.

In addition, a sealing member configured to seal the sterilizing space may be disposed between the main body and the moving part.

In addition, the sterilizing space may contain sterilizing water sterilizing the water outlet, and at least a portion of the water outlet may be submerged in the sterilizing water.

In addition, the sterilizing water generated in a sterilizing water generation unit included in the water treatment part and discharged through the water outlet may be contained in the sterilizing space for a predetermined period of time.

In addition, a sterilizing water discharge line configured to discharge the sterilizing water contained in the sterilizing space may be connected to the sterilizing space, and an interior diameter of the water outlet may be greater than an interior diameter of the sterilizing water discharge line.

In addition, the sterilizing water discharge line may be connected to an upper side surface or an upper surface of the sterilizing space.

In addition, a residual sterilizing water discharge line configured to prevent the sterilizing water from remaining in the sterilizing space after sterilizing the water outlet may be connected to the sterilizing space.

In addition, the interior diameter of the sterilizing water discharge line may be greater than an interior diameter of the residual sterilizing water discharge line.

In addition, a cross-sectional area of the water outlet may be greater than a sum of a cross-sectional area of the sterilizing water discharge line and a cross-sectional area of the residual sterilizing water discharge line.

In addition, the residual sterilizing water discharge line may be connected to a lower surface of the sterilizing space.

In addition, the sterilizer may further include a tray member in which the sterilizing space is formed, movably disposed in the main body.

In addition, a sealing member having a fitting hole into which the water outlet is fitted to be sealed may be disposed at an upper opening of the tray member.

In addition, a residual sterilizing water discharge line configured to prevent the sterilizing water from remaining in the sterilizing space after sterilizing the water outlet may be connected to the tray member.

In addition, an interior diameter of the water outlet may be greater than an interior diameter of the residual sterilizing water discharge line.

In addition, the residual sterilizing water discharge line may be connected to a lower surface of the tray member.

In addition, the sterilizer may further include an ultraviolet irradiation unit configured to emit ultraviolet light to the sterilizing space.

According to an aspect of the present disclosure, a water treatment apparatus may include a main body, a water treatment part configured to treat raw water flowing thereinto and disposed in the main body, and a sterilizing structure of a water outlet device. The sterilizing structure of the water outlet device may include a water outlet configured to discharge treated water treated in the water treatment part externally, and a sterilizer configured to sterilize the water outlet.

In this case, the water treatment apparatus may further include a moving part movably disposed in the main body, and the water outlet may be disposed in the moving part.

Also, the moving part may be movably disposed on the main body.

In addition, the sterilizer may be disposed in at least one of the main body and the moving part.

In addition, the sterilizer may include a sterilizing space in which the water outlet is sterilized.

In addition, the water treatment part may include a water filter configured to filter water.

In addition, the water treatment part may include a storage tank configured to store treated water.

In addition, the water treatment part may include a sterilizing water generation unit, configured to generate sterilizing water, sterilizing the water outlet and supply the sterilizing water to the water outlet.

Advantageous Effects

As set forth above, according to an exemplary embodiment in the present disclosure, a water outlet can be sterilized.

In addition, according to an exemplary embodiment in the present disclosure, contamination of the water outlet can be minimized.

In addition, according to an exemplary embodiment in the present disclosure, exposure of the water outlet externally can be minimized.

In addition, according to an exemplary embodiment in the present disclosure, sanitary properties of the water outlet can be improved.

DESCRIPTION OF DRAWINGS

FIG. 1 is a diagram illustrating a sterilizing structure of a water outlet device and a water treatment apparatus including the same according to a first exemplary embodiment in the present disclosure;

FIGS. 2 to 4 are diagrams illustrating operations of the sterilizing structure of the water outlet device and the water treatment apparatus including the same according to the first exemplary embodiment in the present disclosure;

FIG. 5 is a diagram illustrating a sterilizing structure of a water outlet device and a water treatment apparatus including the same according to a second exemplary embodiment in the present disclosure;

FIGS. 6 to 8 are diagrams illustrating operations of the sterilizing structure of the water outlet device and the water treatment apparatus including the same according to the second exemplary embodiment in the present disclosure;

FIG. 9 is a diagram illustrating a sterilizing structure of a water outlet device and a water treatment apparatus including the same according to a third exemplary embodiment in the present disclosure;

FIGS. 10 to 12 are diagrams illustrating operations of the sterilizing structure of the water outlet device and the water treatment apparatus including the same according to the third exemplary embodiment in the present disclosure;

MODES FOR CARRYING OUT THE INVENTION

Hereinafter, a sterilizing structure of a water outlet device and a water treatment apparatus including the same according to exemplary embodiments in the present disclosure will be described in more detail as follows.

The present inventive concept may, however, be exemplified in many different forms and should not be construed as being limited to the specific embodiments set forth herein. Rather, these embodiments are provided so that this disclosure will be thorough and complete, and will fully convey the scope of the disclosure to those skilled in the art. Accordingly, it will be apparent to those skilled in the art that various modifications can be made to the exemplary embodiments in the present disclosure without departing from the spirit or scope of the invention. Further, in the accompanying drawings, the same or similar components in or on these embodiments in the present disclosure are designated by the same reference numerals or by these numerals with suffixes, even though they are depicted in different drawings.

First Exemplary Embodiment

Hereinafter, a sterilizing structure of a water outlet device and a water treatment apparatus including the same according to a first exemplary embodiment in the present disclosure will be described with reference to FIGS. 1 to 4.

FIG. 1 is a diagram illustrating the sterilizing structure of the water outlet device and the water treatment apparatus including the same according to the first exemplary embodiment in the present disclosure, and FIGS. 2 to 4 are diagrams illustrating operations of the sterilizing structure of the water outlet device and the water treatment apparatus including the same according to the first exemplary embodiment in the present disclosure.

[Sterilizing Structure of Water Outlet Device]

A sterilizing structure 100 of a water outlet device according to a first exemplary embodiment in the present disclosure may include a water outlet 200 and a sterilizer 300.

The water outlet 200 may discharge treated water, treated in a water treatment apparatus 10, externally. The water outlet 200 may be disposed in a moving part 30 disposed on a main body 20 included in the water treatment apparatus 10, as illustrated in FIG. 1. Accordingly, the water outlet 200 may be exposed or may be not exposed depending on the movement of the moving part 30.

The water outlet 200 may be exposed when the treated water treated in the water treatment apparatus 10 is discharged externally, as illustrated in FIG. 3. In addition, the water outlet 200 may not be exposed when the treated water is not discharged as illustrated in FIG. 2 or when the water outlet 200 is sterilized by the sterilizer 300 as illustrated in FIG. 4.

As described above, since the water outlet 200 is exposed only when the treated water is discharged externally, contamination of the water outlet 200 by external pollutants may be minimized and thereby sanitary properties of the water outlet 200 may be improved. In addition, clearer treated water may be supplied to a user.

Meanwhile, the moving part 30 of the water treatment apparatus 10 may be movably disposed on the main body 20. However, the location of the moving part 30 movably disposed on the main body 20 is not be specifically limited.

That is, the moving part 30 of the water treatment apparatus 10 may be movably disposed in any location of the main body 20.

In addition, the configuration of the moving part 30 movably disposed on the main body 20 is not specifically limited, and any known configuration may be utilized. For example, the moving part 30 may slide on the main body 20, or the moving part 30 may move on the main body 20 in such a manner that one of the moving part 30 and the main body 20 has a moving projection or a rail and the other of the moving part 30 and the main body 20 has a moving groove or a wheel.

A discharge line LWD, connected to a water treatment part 40 disposed in the main body 20 of the water treatment apparatus 10 to treat raw water flowing into the main body 20, may be connected to the water outlet 200.

At least a portion of the discharge line LWD may include a flexible tube. Accordingly, the movement of the moving part 30 of the water treatment apparatus 10 may not be obstructed by the discharge line LWD.

The discharge line LWD may include a discharge valve VWD. In addition, when the discharge valve VWD is closed as illustrated in FIG. 2, the treated water treated in the water treatment part 40 may not be discharged through the water outlet 200. In addition, when the discharge valve VWD is opened as illustrated in FIG. 3, the treated water treated in the water treatment part 40 may be discharged externally through the water outlet 200.

Meanwhile, when the discharge valve VWD is opened, sterilizing water generated in a sterilizing water generation unit 45, which will be described later, included in the water treatment part 40 may flow through the discharge line LWD to be discharged through the water outlet 200, as illustrated in FIG. 4.

A structure and shape of the water outlet 200 is not specifically limited, and any structure and shape known in the art may be utilized as long as it discharges treated water treated in the water treatment apparatus 10 externally. For example, the water outlet 200 may be integrally formed with the discharge line LWD.

The sterilizer 300 may sterilize the water outlet 200. The sterilizer 300 may be disposed in at least one of the main body 20 and the moving part 30 in the water treatment apparatus 10, as illustrated in FIG. 1.

The sterilizer 300 may include a sterilizing space 310. The water outlet 200 may be sterilized in the sterilizing space 310.

The sterilizing space 310 may be formed in at least one of the main body 20 and the moving part 30 in the water treatment apparatus 10. For example, the sterilizing space 310 may be formed in the moving part 30 of the water treatment apparatus 10, as illustrated in FIG. 1. Alternatively, the sterilizing space 310 may be formed in the main body 20 of the water treatment apparatus 10. In addition, a portion of the sterilizing space 310 may be formed in the main body 20 and the other portion of the sterilizing space 310 may be formed in the moving part 30.

A sealing member R may be disposed between the main body 20 and the moving part 30 in the water treatment apparatus 10. The sealing member R may be disposed between the main body 20 and the moving part 30 in a location in which the sterilizing space 310 is formed, as illustrated in FIG. 1. The sterilizing space 310 may be sealed by the sealing member R.

The sealing member R is not specifically limited and any sealing member known in the art may be utilized as long as it seals the sterilizing space 310 between the main body 20 and the moving part 30 in the water treatment apparatus 10.

The sterilizing space 310 may contain sterilizing water sterilizing the water outlet 200 in such a manner that at least a portion of the water outlet 200 is submerged in the sterilizing water. Accordingly, the water outlet 200 may be sterilized by the sterilizing water contained in the sterilizing space 310.

As illustrated in FIG. 4, the sterilizing space 310 may contain the sterilizing water generated in the sterilizing water generation unit 45 belonging to the water treatment part 40 disposed in the water treatment apparatus 10 and discharged through the water outlet 200, for a predetermined period of time.

Meanwhile, the sterilizing space 310 may contain sterilizing water generated from another sterilizing water generating unit besides the sterilizing water generation unit 45 and discharged through the water outlet 200, for a predetermined period of time.

A sterilizing water discharge line LSD through which the sterilizing water contained in the sterilizing space 310 is discharged may be connected to the sterilizing space 310. Accordingly, the sterilizing water that has sterilized the water outlet 200 may be discharged from the sterilizing space 310 through the sterilizing water discharge line LSD. In addition, the sterilizing space 310 may contain fresh sterilizing water discharged through the water outlet 200.

An interior diameter D1 of the water outlet 200 may be greater than an interior diameter D2 of the sterilizing water discharge line LSD. Accordingly, the sterilizing water discharged into the sterilizing space 310 through the water outlet 200 may not be immediately discharged through the sterilizing water discharge line LSD, but be contained in the sterilizing space 310 for a predetermined period of time so that at least a portion of the water outlet 200 is submerged.

In addition, the sterilizing water discharge line LSD may be connected to an upper side surface or an upper surface of the sterilizing space 310.

As illustrated in FIG. 1, one end of the sterilizing water discharge line LSD may be connected to the sterilizing space 310 formed in the moving part 30 of the water treatment apparatus 10, and the other end of the sterilizing water discharge line LSD may be connected to a main discharge line LD disposed in the main body 20 of the water treatment apparatus 10.

Accordingly, the sterilizing water of the sterilizing space 310 flowing into the sterilizing water discharge line LSD may be discharged externally through the main discharge line LD.

In this case, at least a portion of the sterilizing water discharge line LSD may include a flexible tube. Accordingly, the movement of the moving part 30 of the water treatment apparatus 10 may not be obstructed by the sterilizing water discharge line LSD.

A residual sterilizing water discharge line LSR may be connected to the sterilizing space 310. Due to the residual sterilizing water discharge line LSR, the sterilizing water may not remain in the sterilizing space 310 after the water outlet 200 is sterilized by the sterilizing water.

In addition, the sterilizing water remaining in the sterilizing space 310 may not be discharged externally when the moving part 30 of the water treatment apparatus 10 moves to expose the water outlet 200 externally after sterilizing the water outlet 200. Accordingly, areas around the water treatment apparatus 10 may not be contaminated by the sterilizing water.

The residual sterilizing water discharge line LSR may be connected to a lower surface of the sterilizing space 310. In addition, the interior diameter D2 of the sterilizing water discharge line LSD may be greater than an interior diameter D3 of the residual sterilizing water discharge line LSR. In addition, a cross-sectional area of the water outlet 200 may be greater than a sum of a cross-sectional area of the sterilizing water discharge line LSD and a cross-sectional area of the residual sterilizing water discharge line LSR.

Accordingly, the sterilizing water discharged through the water outlet 200 may be contained in the sterilizing space 310 for a predetermined period of time so that at least a portion of the water outlet 200 is submerged in the sterilizing water. In addition, when the sterilizing water does not flow from the water outlet 200 after the water outlet 200 is sterilized, the sterilizing water may be discharged through the sterilizing water discharge line LSD and the residual sterilizing water discharge line LSR. Accordingly, the sterilizing water may not remain in the sterilizing space 310.

The residual sterilizing water discharge line LSR may be connected to the main discharge line LD disposed in the main body 20 of the water treatment apparatus 10. Thereby, the sterilizing water flowing into the residual sterilizing water discharge line LSR from the sterilizing space 310 may be discharged externally through the main discharge line LD.

Meanwhile, a vent line (not illustrated) having a vent valve (not illustrated) may be connected to the sterilizing space 310, thereby discharging air existing in the sterilizing space 310 externally during initial stages of supplying the sterilizing water to the sterilizing space 310.

The vent line may be connected to the upper surface of the sterilizing space 310. In addition, the vent valve may be opened to discharge the air existing in the sterilizing space 310 externally through the vent line during the initial stages of supplying the sterilizing water, and the vent valve may be closed after the air existing in the sterilizing space 310 is completely discharged externally.

[Water Treatment Device]

A water treatment apparatus 10 according the first exemplary embodiment in the present disclosure may include a main body 20, a moving part 30, a water treatment part 40, and the sterilizing structure 100 of the water outlet device described above.

The main body 20 may include components of the water treatment apparatus 10, such as the water treatment part 40. A structure and shape of the main body 20 is not specifically limited, and any structure and shape known in the art may be utilized as long as it includes the components of the water treatment apparatus 10, such as the water treatment part 40.

The moving part 30 may be movably disposed on the main body 20. The moving part 30 may be movably disposed on an upper surface of the main body 20. However, an area of the main body 20 on which the moving part 30 is movably disposed is not specifically limited, and the moving part 30 may be movably disposed on any area of the main body 20.

In addition, the configuration in which the moving part 30 is movably disposed on the main body 20 is not specifically limited, and any configuration known in the art may be utilized. For example, the moving part 30 may slide on the main body 20, or move on the main body 20 in such a manner that one of the moving part 30 and the main body 20 has a moving projection or a rail and the other of the moving part 30 and the main body 20 has a moving groove or a wheel.

The water treatment part 40 may be disposed in the main body 20 to treat raw water flowing thereinto. A raw water line LRW connected to a source of the raw water (not illustrated), such as standpipe, may be connected to the water treatment part 40 to supply the raw water from the source of the raw water.

The raw water line LRW may include a pressure-reducing valve VRP. Accordingly, a pressure of the raw water flowing into the raw water line LRW may be reduced to a predetermined pressure, to allow the raw water to flow into the water treatment part 40.

The water treatment part 40 may include water filters 41, 42, and 43 to filter water. Accordingly, the raw water flowing into water treatment part 40 may be treated by the water filters 41, 42, and 43. The raw water may be filtered by the water filters 41, 42, and 43 to be purified water.

The water filters 41, 42, and 43 included in the water treatment part 40 may include a pre-processing filter 41, a reverse osmosis membrane filter 42, and a post-processing filter 43. However, the water filters 41, 42, and 43 included in the water treatment part 40 are not be specifically limited, and any filters known in the art may be utilized as long as they filter water.

The pre-processing filter 41, the reverse osmosis membrane filter 42, and the post-processing filter 43 may be connected to each other by a connection line LC. In addition, the pre-processing filter 41 may be connected to the raw water line LRW by the connection line LC. In addition, the connection line LC connecting the pre-processing filter 41 to the reverse osmosis membrane filter 42 may include a first supply valve V1.

Accordingly, when the first supply valve V1 is opened, the raw water flowing into the water treatment part 40 through the raw water line LRW may be sequentially filtered by the pre-processing filter 41, the reverse osmosis membrane filter 42, and the post-processing filter 43, as illustrated in FIG. 2.

A domestic water line LLV may be connected to the reverse osmosis membrane filter 42. Accordingly, domestic water that has not been filtered by the reverse osmosis membrane filter 42 may be discharged from the reverse osmosis membrane filter 42 through the domestic water line LLV.

The connection line LC connecting the reverse osmosis membrane filter 42 to the post-processing filter 43 may include a check valve VC. Accordingly, treated water treated in the reverse osmosis membrane filter 42 may be prevented from flowing back into the reverse osmosis membrane filter 42 instead of flowing into the post-processing filter 43.

The domestic water line LLV may include a domestic water valve VLV. The domestic water valve VLV may function to maintain a predetermined pressure so that the raw water is filtered by the reverse osmosis membrane filter 42.

The domestic water line LLV may include a check valve VC. Accordingly, the domestic water flowing through the domestic water line LLV may be prevented from flowing back into the reverse osmosis membrane filter 42.

The domestic water line LLV may be connected to the main discharge line LD. The main discharge line LD may include a main discharge valve VD.

Accordingly, the domestic water flowing through the domestic water line LLV may be discharged externally through the main discharge line LD when the main discharge valve VD is opened, as illustrated in FIG. 2.

The water treatment part 40 may include a storage tank 44. The treated water may be stored in the storage tank 44.

The storage tank 44 may include an external tank 44a from which or into which the raw water or the domestic water flows, and an inside tank 44b from which or into which the treated water flows, as illustrated in FIG. 1. The inside tank 44b may be disposed in the external tank 44a. The inside tank 44b may include a material stretched and contracted according to inflow and outflow of the treated water. For example, the inside tank 44b may include vinyl.

The external tank 44a may be connected to the domestic water line LLV and the main discharge line LD by a pressure-applying line LAP. In addition, the raw water line LRW may be connected to the main discharge line LD by a discharge connection line LDC. In addition, the discharge connection line LDC may include a second supply valve V2. In addition, the inside tank 44b may be connected to the connection line LC connected to the post-processing filter 43 by a supply line LPV.

Thus, the treated water filtered by the water filters 41, 42, and 43 may flow into the inside tank 44b through the supply line LPV and stored in the inside tank 44b, as illustrated in FIG. 2. In addition, the raw water or domestic water existing in the external tank 44a may be flow into the main discharge line LD via the pressure-applying line LAP to be discharged externally.

In addition, when the second supply valve V2 and the main discharge valve VD are opened in a state in which the treated water is stored in the inside tank 44b, the raw water may be supplied to the external tank 44a via the discharge connection line LDC, the main discharge line LD, and the pressure-applying line LAP, as illustrated in FIG. 3. In addition, the domestic water may be supplied to the external tank 44a via the domestic water line LLV and the pressure-applying line LAP.

Thus, the treated water stored in the inside tank 44b may be discharged externally via the supply line LPV, the discharge line LWD, and the water outlet 200, and supplied to a user, as illustrated in FIG. 3.

Due to such configuration, the treated water treated in the water treatment part 40 may be easily supplied to the water outlet 200 located in the moving part 30 disposed on the main body 20 without a pressure-applying tool such as a pump.

The water treatment part 40 may include a sterilizing water generation unit 45. The sterilizing water generation unit 45 may generate sterilizing water sterilizing the water outlet 200. In addition, the sterilizing water generated in the sterilizing water generation unit 45 may be supplied to the water outlet 200.

The sterilizing water generation unit 45 may generate sterilizing water by electrolysis, for example. However, the configuration of the sterilizing water generation unit 45 generating the sterilizing water is not specifically limited, and any configuration known in the art, e.g. a configuration in which sterilizing water is generated by dissolving a sterilizing agent in raw water or treated water, may be utilized.

The sterilizing water generation unit 45 may be connected to the raw water line LRW by the connection line LC. The connection line LC connecting the sterilizing water generation unit 45 to the raw water line LRW may include a third supply valve V3.

Accordingly, when the third supply valve V3 is opened, the raw water is supplied to the sterilizing water generation unit 45 to generate the sterilizing water, as illustrated in FIG. 4.

The sterilizing water generation unit 45 may be connected to the discharge line LWD by a sterilizing water line LST. In addition, when the third supply valve V3 and the discharge valve VWD are opened in a state in which the first supply valve V1 is closed, the sterilizing water generated in the sterilizing water generation unit 45 may be supplied to the water outlet 200 through the sterilizing water line LST and the discharge line LWD and discharged through the water outlet 200, as illustrated in FIG. 4.

Since the sterilizing structure 100 of the water outlet device has been already described above, descriptions thereof will be omitted.

Second Exemplary Embodiment

Hereinafter, a sterilizing structure of a water outlet device and a water treatment apparatus including the same according to a second exemplary embodiment in the present disclosure will be described with reference to FIGS. 5 to 8.

FIG. 5 is a diagram illustrating the sterilizing structure of the water outlet device and the water treatment apparatus including the same according to the second exemplary embodiment in the present disclosure, and FIGS. 6 to 8 are diagrams illustrating the operation of the sterilizing structure of the water outlet device and the water treatment apparatus including the same according to the second exemplary embodiment in the present disclosure.

Here, there is a difference between the sterilizing structure of the water outlet device and the water treatment apparatus including the same according to the second exemplary embodiment and the sterilizing structure of the water outlet device and the water treatment apparatus including the same according to the first exemplary embodiment described above with reference to FIGS. 1 to 4, in that a sterilizer 300 according to the second exemplary embodiment further includes a tray member 320.

Therefore, components different from those of the first exemplary embodiment will be mainly described, and other components described above with reference to FIGS. 1 to 4 will be omitted.

As illustrated in FIG. 5, the sterilizer 300 of the sterilizing structure 100 of the water outlet device according to the second exemplary embodiment in the present disclosure may further include the tray member 320.

A sterilizing space 310 may be formed in the tray member 320. In addition, the tray member 320 may be movably disposed on a main body 20.

The configuration in which the tray member 320 is movably disposed on the main body 20 is not specifically limited, and any configuration known in the art, such as a configuration in which the tray member 320 is movably disposed by a hydraulic cylinder or a feed screw, and a motor connected thereto, may be utilized.

Accordingly, when treated water is stored in an inside tank 44b of a storage tank 44, or the treated water stored in the inside tank 44b is discharged through a water outlet 200, the tray member 320 may move, e.g. descend, to a position in which the water outlet 200 is not located in the sterilizing space 310, as illustrated in FIGS. 6 and 7.

In addition, when the water outlet 200 is sterilized, the tray member 320 may move, e.g. ascend, to a position at which the water outlet 200 is located in the sterilizing space 310, as illustrated in FIG. 8.

A sealing member 321 having a fitting hole 321a may be disposed in an upper opening of the tray member 320. The water outlet 200 may be fitted into the fitting hole 321a of the sealing member 321, as illustrated in FIG. 8.

Accordingly, the sterilizing space 310 formed in the tray member 320 may be sealed. In addition, when sterilizing water is discharged through the water outlet 200 and contained into the sterilizing space 310, the sterilizing water may not be discharged externally of the tray member 320, as illustrated in FIG. 8.

A residual sterilizing water discharge line LSR may be connected to the tray member 320. The residual sterilizing water discharge line LSR may be connected to a lower surface of the tray member 320.

Accordingly, the sterilizing water that has sterilized the water outlet 200 may be discharged from the sterilizing space 310 through the residual sterilizing water discharge line LSR. In addition, fresh sterilizing water discharged through the water outlet 200 may be contained in the sterilizing space 310. In addition, the sterilizing water may not remain in the sterilizing space 310 of the tray member 320 after the water outlet 200 is sterilized.

At least a portion of the residual sterilizing water discharge line LSR may include a flexible tube. Accordingly, the movement of the tray member 320 may not be obstructed by the residual sterilizing water discharge line LSR.

An interior diameter D1 of the water outlet 200 may be greater than an interior diameter D3 of the residual sterilizing water discharge line LSR. Accordingly, while the sterilizing water discharged through the water outlet 200 is contained in the sterilizing space 310 of the tray member 320 in such manner that at least a portion of the water outlet 200 is submerged in the sterilizing water, the sterilizing water may not remain in the sterilizing space 310 after the water outlet 200 is sterilized.

Third Example Embodiment

Hereinafter, a sterilizing structure of a water outlet device and a water treatment apparatus including the same according to a third exemplary embodiment in the present disclosure will be described with reference to FIGS. 9 to 12.

FIG. 9 is a diagram illustrating the sterilizing structure of the water outlet device and the water treatment apparatus including the same according to the third exemplary embodiment in the present disclosure, and FIGS. 10 to 12 are diagrams illustrating the operation of the sterilizing structure of the water outlet device and the water treatment apparatus including the same according to the third exemplary embodiment in the present disclosure.

Here, there is a difference between the sterilizing structure of the water outlet device and the water treatment apparatus including the same according to the third exemplary embodiment and the sterilizing structure of the water outlet device and the water treatment apparatus including the same according to the first exemplary embodiment described above with reference to FIGS. 1 to 4, in that a sterilizer 300 according to the third exemplary embodiment further includes an ultraviolet irradiation unit 330 emitting ultraviolet light to a sterilizing space 310.

Therefore, components different from those of the first exemplary embodiment will be mainly described, and other components described above with reference to FIGS. 1 to 4 will be omitted.

As illustrated in FIG. 9, the sterilizer 300 of the sterilizing structure of the water outlet device according to the third exemplary embodiment in the present disclosure may further include the ultraviolet irradiation unit 330.

The ultraviolet irradiation unit 330 may emit ultraviolet light to the sterilizing space 310. The ultraviolet irradiation unit 330 may emit ultraviolet light to the sterilizing space 310 when a water outlet 200 is sterilized, as illustrated in FIG. 12. Accordingly, the water outlet 200 may be sterilized by the ultraviolet light emitted from the ultraviolet irradiation unit 330.

However, when treated water is stored in an inside tank 44b of a storage tank 44 or the treated water stored in the inside tank 44b is discharged through the water outlet 200, the ultraviolet irradiation unit 330 may not emit the ultraviolet light to the sterilizing space 310, as illustrated in FIGS. 10 and 11.

The ultraviolet irradiation unit 330 is not specifically limited, and any ultraviolet irradiation unit, such as an ultraviolet LED, known in the art may be utilized as long as it emits ultraviolet light.

Meanwhile, when the water outlet 200 is sterilized by the ultraviolet light emitted from the ultraviolet irradiation unit 330 to the sterilizing space 310 as described above, a water treatment part 40 of a water treatment apparatus 10 according to the third exemplary embodiment in the present disclosure may not include a sterilizing water generation unit 45 supplying sterilizing water to the water outlet 200 and associated configurations, as illustrated in FIG. 9.

However, the ultraviolet irradiation unit 330 may be included in the sterilizer 300 disposed in the sterilizing structure of the water outlet device and the water treatment apparatus including the same according to the first exemplary embodiment or second exemplary embodiment in the present disclosure.

As set forth above, by using the sterilizing structure of the water outlet device and the water treatment apparatus including the same according to the exemplary embodiments in the present disclosure, the water outlet may be sterilized and the contamination of the water outlet may be minimized. Further, the exposure of the water outlet externally may be minimized and sanitary properties of the water outlet may be improved.

While exemplary embodiments have been shown and described above, it will be apparent to those skilled in the art that modifications and variations could be made without departing from the scope of the invention as defined by the appended claims.

The invention claimed is:

1. A sterilizing structure of a water outlet device comprising:
    a water outlet configured to discharge treated water, treated in a water treatment apparatus, externally; and
    a sterilizer sterilizing the water outlet,
    wherein the water outlet is located in a moving part configured to move on a main body included in the water treatment apparatus,
    wherein the sterilizer includes a sterilizing space in which the water outlet is sterilized, and
    wherein the sterilizing space contains sterilizing water sterilizing the water outlet, and at least a portion of the water outlet is submerged in the sterilizing water.

2. The sterilizing structure of the water outlet device of claim 1, wherein the sterilizer is located in at least one of the main body and the moving part.

3. The sterilizing structure of the water outlet device of claim 1, wherein the sterilizing water generated in a sterilizing water generation unit included in the water treatment part and discharged through the water outlet is contained in the sterilizing space for a predetermined period of time.

4. The sterilizing structure of the water outlet device of claim 3, wherein a sterilizing water discharge line configured to discharge the sterilizing water contained in the sterilizing space is connected to the sterilizing space, and an interior diameter of the water outlet is greater than an interior diameter of the sterilizing water discharge line.

5. The sterilizing structure of the water outlet device of claim 4, wherein a residual sterilizing water discharge line configured to prevent the sterilizing water from remaining in the sterilizing space after sterilizing the water outlet is connected to the sterilizing space.

6. The sterilizing structure of the water outlet device of claim 5, wherein the interior diameter of the sterilizing water discharge line is greater than an interior diameter of the residual sterilizing water discharge line.

7. The sterilizing structure of the water outlet device of claim 6, wherein a cross-sectional area of the water outlet is greater than a sum of a cross-sectional area of the sterilizing water discharge line and a cross-sectional area of the residual sterilizing water discharge line.

8. The sterilizing structure of the water outlet device of claim 5, wherein the residual sterilizing water discharge line is connected to a lower surface of the sterilizing space.

9. The sterilizing structure of the water outlet device of claim 3, wherein the sterilizer further includes a tray member in which the sterilizing space is formed, movably disposed in the main body.

10. The sterilizing structure of the water outlet device of claim 9, wherein a sealing member having a fitting hole into which the water outlet is fitted to be sealed is disposed at an upper opening of the tray member.

11. The sterilizing structure of the water outlet device of claim 10, wherein a residual sterilizing water discharge line configured to prevent the sterilizing water from remaining in the sterilizing space after sterilizing the water outlet is connected to the tray member.

12. The sterilizing structure of the water outlet device of claim 11, wherein an interior diameter of the water outlet is greater than an interior diameter of the residual sterilizing water discharge line.

13. The sterilizing structure of the water outlet device of claim 11, wherein the residual sterilizing water discharge line is connected to a lower surface of the tray member.

14. The sterilizing structure of the water outlet device of claim 1, wherein a sealing member configured to seal the sterilizing space is disposed between the main body and the moving part.

15. The sterilizing structure of the water outlet device of claim 1, wherein a sterilizing water discharge line is connected to the sterilizing space so that the sterilizing water contained in the sterilizing space is discharged, and the sterilizing water discharge line is disposed above the end of the water outlet.

16. A water treatment apparatus, comprising:
a main body;
a water treatment part configured to treat raw water flowing thereinto and disposed in the main body;
a sterilizing structure of a water outlet device including a water outlet configured to discharge treated water treated in the water treatment part externally, and a sterilizer configured to sterilize the water outlet; and
a moving part movably disposed in the main body,
wherein the water outlet is disposed in the moving part,
wherein the sterilizer includes a sterilizing space in which the water outlet is sterilized, and
wherein the sterilizing space contains sterilizing water sterilizing the water outlet, and at least a portion of the water outlet is submerged in the sterilizing water.

17. The water treatment apparatus of claim 16, wherein the sterilizer is disposed in at least one of the main body and the moving part.

* * * * *